United States Patent [19]

Nelson et al.

[11] 4,417,571

[45] Nov. 29, 1983

[54] PROSTHETIC CEMENT SPACER AND METHOD FOR USING SAME

[76] Inventors: Carl L. Nelson, 4301 W. Markham, Little Rock, Ark. 72201; Darrel W. Haynes, 11200 Bainbridge Dr., Little Rock, Ark. 72212; Michael J. Weber, Rte. 3, Box 410B, Little Rock, Ark. 72211

[21] Appl. No.: 205,455

[22] Filed: Nov. 10, 1980

Related U.S. Application Data

[62] Division of Ser. No. 54,027, Jul. 2, 1979, Pat. No. 4,285,071.

[51] Int. Cl.³ .............................................. A61F 1/24
[52] U.S. Cl. ................................ 128/92 B; 411/377; 411/903; 3/1.9; 3/1.912; 128/92 CA
[58] Field of Search .................... 3/1, 1.9, 1.91, 1.912, 3/1.913; 128/92 C, 92 CA, 92 B, 92 BA, 92 D; 428/120; 156/330

[56] References Cited

U.S. PATENT DOCUMENTS

| | | | |
|---|---|---|---|
| 2,839,815 | 6/1958 | Reeves et al. | 128/92 B |
| 3,528,109 | 9/1970 | Scales | 128/92 C |
| 3,558,422 | 1/1971 | Hamilton et al. | 156/330 |

Primary Examiner—Richard J. Apley
Assistant Examiner—David J. Isabella
Attorney, Agent, or Firm—Woodard, Weikart, Emhardt & Naughton

[57] ABSTRACT

A prosthetic cement spacer for controlling the thickness of cement applied between a prosthetic insert and a support member, such as an acetabulum, includes a generally cylindrical standoff body portion fabricated from acrylic bone cement and a pointed wire concentric with said standoff body and outwardly extending from one end a sufficient length to anchor into the acetabulum bone surface. The method of use of these prosthetic cement spacers involves preparation of the acetabulum so that there is sufficient clearance space for the prosthetic cement spacers and then to insert the pointed wires into the acetabulum bone surface in an equilateral triangular arrangement thereby providing three points of contact for the prosthetic insert, such as an acetabular cup. By selecting three prosthetic cement spacers all having substantially the same standoff body height, the clearance region between the acetabulum bone surface and the acetabular cup is controlled and provides a uniform cement thickness throughout thereby providing an improved bonding arrangement.

1 Claim, 6 Drawing Figures

PROSTHETIC CEMENT SPACER AND METHOD FOR USING SAME

This is a division of application Ser. No. 54,027, filed July 2, 1979, now U.S. Pat. No. 4,285,071.

BACKGROUND OF THE INVENTION

This invention relates in general to prosthetic devices and in particular to a device and method for securing a prosthetic insert to a support member, such as a natural bone.

Prosthetic devices for the replacement of damaged or deteriorating portions of anatomy are well known in the art and are not necessarily restricted by the particular nature of the anatomy which needs replacing. Prosthetic devices range from full limb replacement types to those for small joint and bone replacements and regardless of their particular shape and size, one criteria of all prosthetic devices is that there is a need to secure the prosthetic device in place so that it functions properly.

Certain prosthetic devices which insert into the intramedullary canal of a bone may incorporate surface contouring to aid in this securing, and although cement may also be used, a primary contributor to the overall rigidity of the prosthesis is the surface contouring. Typical of this type of device are femoral head prostheses which insert into the shaft of the femur. However, there are certain areas of the anatomy which may need replacement of reconstruction and which do not have either the shape or bone mass for receiving an inserted prosthetic portion. Consider the innominate bone and in particular, the acetabulum. When both parts of the ball and socket full hip joint connection need replacement or reconstruction, the femoral head must be replaced with a prosthetic ball-shaped member and the acetabulum must be lined with a socket or cup member in order to receive this ball-shaped member. One method of affixing this acetabular cup into the acetabulum is by a layer of acrylic cement packed between the acetabulum and the acetabular cup.

While a variety of prosthetic devices for hip joint replacement and repair are known in the art, none of these prior art devices nor their corresponding method of use achieve the desirable results which the present invention achieves. The following listed patents provide an indication of some of these prior art prosthetic devices and methods.

| Patent No. | Patentee | Issue Date |
| --- | --- | --- |
| 4,092,741 | David | 6/06/78 |
| 3,740,769 | Haboush | 6/26/73 |
| 3,641,590 | Michele | 2/15/72 |
| 3,521,302 | Muller | 7/21/70 |
| 3,683,421 | Martinie | 8/15/72 |
| 3,656,184 | Chambers | 4/18/72 |

David discloses a prosthetic device for use as a hip joint which includes a substantially spherical portion locatable in the acetabular fossa of a pelvis bone, and a longitudinal portion locatable in a thigh bone. The spherical portion is anchored within the fossa by a holding member which is fixed to the fossa. The FIG. 2 embodiment discloses a cup which is anchored to the pelvis bone by three threaded fasteners.

Haboush discloses a prosthesis for hip joints which is formed as a one-piece unit and includes a spike-like stem that is inserted axially into the femur. An arm integral with the upper end of the stem projects outwardly at an obtuse angle relative to it and a ball is attached at the outer end of the arm connecting the prosthesis to the acetabulum or artificial socket, whichever is used. The ball and socket interface includes a series of Teflon plugs to aid in lubricating the sliding movement between these two surfaces.

Michele discloses a selective, individualized technique for acetabulum socket replacement including use in conjunction with a hip replacement prosthesis for a total hip replacement. The prosthetic portion is anchored into the bone by a main pin and one or more auxiliary pins.

Muller discloses an artificial joint which is formed by a pair of substantially complementary-shaped prosthetic members which have a resiliently compressible slide member disposed between them. The resiliently compressible slide member maintains the prosthetic members in spaced relation when in an unladen state but allows the prosthetic members to contact each other when in a laden state.

Martinie discloses a prosthetic joint assembly for supporting first and second bone members for relative movement between such members. The joint assembly includes a pin member adapted to seat in a pocket formed in the first bone member and a socket assembly adapted to be mounted in the second bone member. Furthermore, there is a connecting member connected at one end to the pin member and having at its opposite end a ball journalled in the socket assembly. The socket assembly attaches to the bone by a layer of acrylic material which appears to be preformed prior to locating it in the reamed and contoured bone.

Chambers discloses an artificial hip joint comprising a socket member and an inter-fitting ball member, in which dislocation of the joint is positively prevented by retaining means forming part of the socket member. The retaining means are constituted by extensions of the socket member beyond its diametral plane which define an opening into the socket smaller than that of the socket at the diametral plane. The socket includes ribs which are engaged by the plastic cement that secures the socket to the bone.

A further prior art disclosure is provided by pages D15 and D16 of a Zimmer Catalog. These pages discuss the procedure of bone preparation and prosthetic implant for a total hip replacement. Once the acetabulum is prepared by reaming, four holes are drilled into the bone and filled with acrylic cement prior to the coating of the acetabulum area with securing cement.

The prior art devices which do use an acrylic cement to secure the prosthetic cup to the acetabulum do not disclose a simple an effective means to control cement thickness. Although the ideal thickness of the cement is not necessarily agreed upon by all orthopedists, most orthopedists do generally concur with the concept that the amount of cement between the prosthetic insert (acetabular cup) and the support member (acetabulum) should be predictable and of a uniform thickness throughout the interface region. Another feature of the prosthesis implanting procedure which many orthopedists agree upon is that the acetabular cup should not rest directly on the bone surface of the acetabulum.

The invention disclosed herein provides a cement spacer concept and method for use with prosthetic inserts for controlling the uniformity and thickness of the cement which is applied between the prosthetic insert and its supporting bone member.

SUMMARY OF THE INVENTION

A prosthetic cement spacer for controlling the thickness of cement applied between a prosthetic insert and a support member to which the insert is to be secured according to one embodiment of the present invention comprises a standoff body having a top surface and base surface and means for anchoring the standoff body to the supporting member, the anchoring means extending outwardly from the base surface.

A method of securing a prosthetic insert to a support member wherein the thickness of the cement applied between the prosthetic insert and the support member is controlled by spacers positioned between the support member and the prosthetic insert according to another embodiment of the present invention comprises the steps of selecting a plurality of spacers, each of which have a standoff body of substantially the same height and a pointed wire outwardly extending from the standoff body, positioning each standoff body against the supporting member by fully inserting the wires into the supporting member, filling the area of separation between the supporting member and the prosthetic insert with cement and placing the prosthetic insert against the outermost ends of the standoff bodies.

One object of the present invention is to provide a prosthetic cement spacer and a method of use which improve the overal cementing procedure of a prosthetic insert to a supporting member.

Related objects and advantages of the present invention will be apparent from the following description.

DESCRIPTION OF THE PREFERRED EMBODIMENTS

Figure 1:
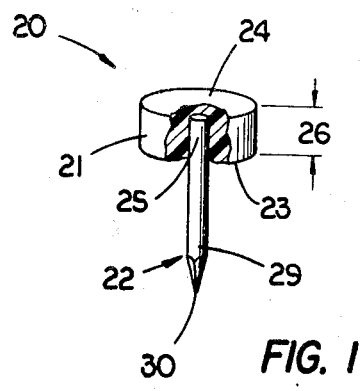
FIG. 1 is a fragmentary perspective view of a prosthetic cement spacer according to a typical embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated a prosthetic cement spacer 20 which includes a generally cylindrical standoff body portion 21 and a pointed wire 22 which extends outwardly from the base surface 23 and is generally concentric therewith. Top surface 24 is substantially flat and generally parallel to base surface 23. Body portion 21 is solid throughout and is secured to the top portion 25 of pointed wire 22 by a suitable anchoring technique. In the exemplary embodiment, this anchoring is accomplished by a molding body portion 21 around top portion 25. The length of top portion 25 is such that it extends for substantially the full length (or height) 26 of body portion 21. The lower portion 29 of pointed wire 22 extends outwardly from base surface 23 a length of approximately 5 mm and end 30 is pointed by a suitable sharpening, drawing or grinding procedure.

Although the initial shape of prosthetic cement spacer 20 is as has been described, it is to be understood that the material used for molding body portion 21 is of a nature and composition that permits it to be easily modified by an orthopedist at the time this cement spacer is being utilized as part of a prosthetic replacement procedure. As will be described in greater detail hereinafter, it is pointed wire 22 which is inserted into a supporting member such as a bone and in the exemplary embodiment, the bone surface of the acetabulum. Therefore, in order to properly seat prosthetic cement spacer 20 against this bone surface, base surface 23 may be slightly contoured or shaped in some manner in order to fit flush against the bone surface. However, inasmuch as the overall size and in particular, the outside diameter of body portion 21 is quite small, base surface 23 normally fits substantially flush with the bone surface to which it is applied without any contouring or shaping. Only in extreme cases of contour irregularities will there be a need to modify the end configuration of prosthetic cement spacer 20. Although dimensions are often a matter of design choice, depending on the specific construction of the device and its intended application, it is to be understood that the dimensional aspects of prosthetic cement spacer 20 are of some importance. The spacers must be small enough so as to provide the benefits of point supports rather than area supports and thus be more suitable for a variety of receiving bone shapes. At the same time pointed wire 22 must be of a sufficient diameter and length to properly secure the spacer into the supporting member. In the exemplary embodiment, the height 26 of body portion 21 is approximately 3 mm and the diameter of body portion 21 is approximately 5 mm. The diameter of pointed wire along its cylindrical body is approximately 0.75 mm. While moderate range variations are permitted to these stated dimensions, it is to be understood that the length of lower portion 29 of wire 22 should be at least as great as the length of top portion 25 and that top portion 25 should extend for substantially the full height 26 of body portion 21.

Figure 2:
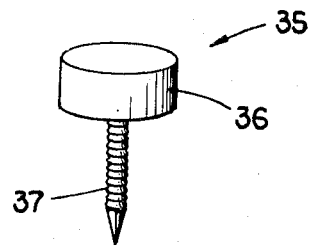
FIG. 2 is a perspective view of an alternate prosthetic cement spacer according to a typical embodiment of the present invention.

Referring to FIG. 2, an alternative prosthetic cement spacer 35 is illustrated. Prosthetic cement spacer 35 includes a standoff body portion 36 similar to body portion 21 but a somewhat different pointed wire 37. The outside diameter of pointed wire 37 is modified with a rolled thread contour and this arrangement permits the spacer to be either pressed or threaded into the supporting member bone and has greater holding power due to this surface contouring. This alternative style is a more appropriate choice in those situations where the supporting member either by its size or its general composition does not appear to provide sufficient holding power for a smooth pointed wire. It should be noted also that while standoff body portions 21 and 36 are preferably molded about the corresponding top portions of their respective pointed wires 22 and 37, this particular fabrication technique is not required. It is conceivable that standoff body portions 21 and 36 could be cut from round bar stock and that the pointed wires could be force inserted into these cylindrical portions. It is also envisioned that different mold shapes could be employed to produce different standoff body portion configurations and such alternatives fall within the intended scope of this invention. The preference of a circular (or cylindrical) shape is that this provides the maximum amount of supporting surface area for top surface 24 with a minimum outside perimeter length being required. Similarly, the smaller the overall area of top surface 24, the more closely this surface will correspond to a point support and thereby not be subject to incompatibilities in contacting contours.

Figure 3:
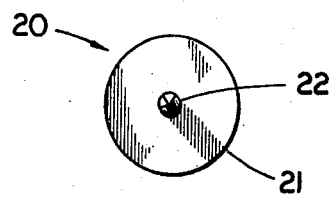
FIG. 3 is a plan view of the underside of the FIG. 1 prosthetic cement spacer.

FIG. 3 illustrates the concentric nature of pointed wire 22 with respect to standoff body portion 21. While this again is the preferred arrangement, it is envisioned that with various shaped standoff body portions the pointed wire may be preferably located in a nonconcentric manner or in some instances there may in fact be more than one pointed wire utilized. For example, it is anticipated that an annular ring spacer might be fabricated as a one-piece unit and thus three or four pointed wires might be required around this annular ring shape in order to adequately support and anchor it against the supporting member, such as the acetabulum bone surface.

Figure 4:
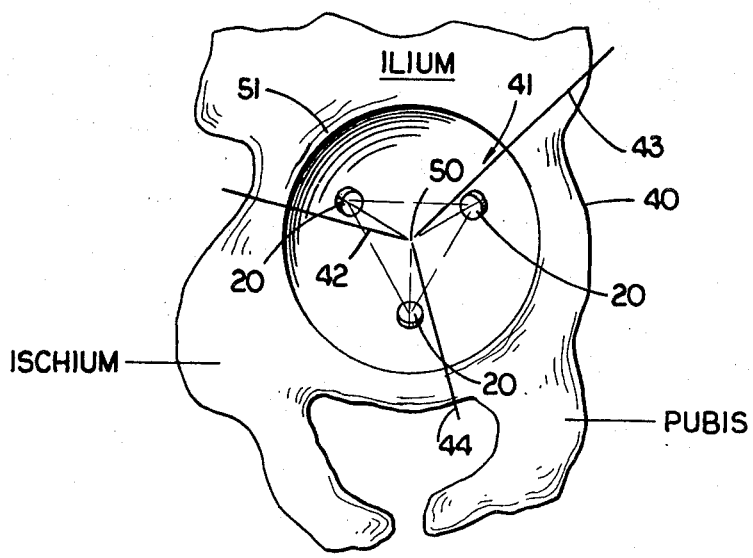
FIG. 4 is a diagrammatic view of an acetabulum with a plurality of FIG. 1 prosthetic cement spacers inserted therein.
Figure 5:
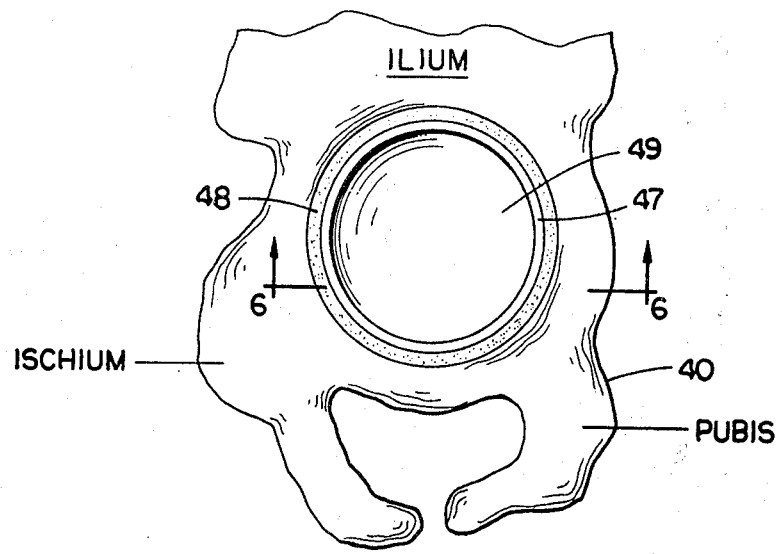
FIG. 5 is a diagrammatic view of the FIG. 4 acetabulum with a prosthetic acetabular cup positioned over the cement spacers.

Referring to FIGS. 4 and 5, the method of use for prosthetic cement spacer 20 is also illustrated. FIG. 4 is a diagrammatic representation of an innominate bone 40 with the acetabulum 41 located therein. Labels for the ischium, ilium and pubis have been applied directly to their corresponding portions in FIG. 4 and the lines of union between these three fused bones are designated as lines 42, 43 and 44. When these is to be a prosthetic replacement of the total hip joint including the femoral head as well as the acetabulum, both of these ball and socket members must be replaced or in some manner modified by prosthetic devices. It is well known in the art to remove the existing natural bone femoral head and to replace this with a prosthetic femoral head which inserts into the intramedullary canal of the shaft of the femur. Since replacement of the entire innominate bone is not achievable nor necessary, all that must be done to provide a compatible socket member for the prosthetic ball is to provide an acetabular cup or socket member in order to receive the head of the femoral prosthetic member. Therefore, it is a requirement to position the acetabular cup within the acetabulum and secure it in place such as by the use of an interface layer of cement. While the ideal thickness of cement is not necessarily agreed upon by all orthopedists, orthopedists generally concur with the concept that the amount of cement between the prosthetic insert (acetabular cup) and the supporting member (acetabulum) should be predictable and of a uniform thickness throughout the interface region. Another feature of the prosthesis implanting procedure which most orthopedists agree upon is that the acetabular cup should not rest directly on the bone surface of the acetabulum.

It should be fairly apparent that prior procedures of attempting to coat the acetabulum with cement and then to place the acetabular cup in position is subject to great irregularities both as to cement thickness as well as with respect to the position and alignment of the acetabular cup. Therefore, the disclosed prosthetic cement spacers provide a quick and reliable means of controlling the cement thickness throughout the interface region. Inasmuch as one of the functions of the prosthetic cement spacers is to provide a firm surface on which the acetabular cup may rest without rocking, a minimum of three cement spacers, arranged in an equilateral triangle shape, are deemed to be the preferred choice. By arranging three cement spacers in such an equilateral triangle arrangement, the acetabular cup may be readily positioned and firmly supported. In the event there is slight rocking or misalignment, the design and construction of the cement spacers permits easy removal and reinsertion at a slightly different location in order to correct this misalignment or rocking. Also, as previously discussed, the material composition of the standoff body portion is such that if the contour of the member needs to be modified by shaving or sanding, this may be done quite easily by the orthopedist at the time of prosthetic implanting.

Figure 6:
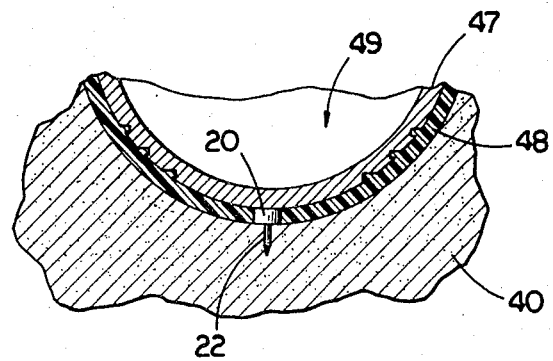
FIG. 6 is a section view of the FIG. 5 acetabular cup as cemented to the acetabulum as taken along line 6—6 in FIG. 5.

FIG. 5 is a diagrammatic representation of the acetabular cup 47 as positioned on the three prosthetic cement spacers 20 with the thickness of cement 48 appearing as a concentric annular ring about the acetabular cup and it is to be understood that this cement thickness is uniform throughout the interface region as is further illustrated by the section view of FIG. 6. The open center 49 of acetabular cup 47 is that region which accepts the ball head of the femoral prosthetic member. Cutting line 6—6 provides the plane of view for the section view of FIG. 6 and thus only the lowermost cement insert 20 of the FIG. 4 illustration is visible. By selecting three prosthetic cement spacers 20 which all have substantially identical heights 26, this uniformity of cement 48 spacing between the acetabulum bone surface and the acetabular cup is preserved throughout, as can be seen. Once the three cement spacers have been positioned such that the acetabular cup does not rock but rather remains steady, it should also be understood that the cup 47 is allowed to slide across the top surfaces 24 of these cement spacers and thereby allow the orthopedist to achieve proper alignment in a firm and positive manner while still holding the acetabular cup firmly against the top surfaces of these cement spacers. Thus, when final alignment is achieved, the cement may be added to the interface spacing to secure the prosthetic acetabular cup into the acetabulum. While this description of the apparatus and its association with the particular anatomy discloses the general mode of utilization of the prosthetic cement spacers, the overall method of use and the surgical procedure is also of interest and the method disclosed hereinafter is tied in closely with the prosthetic cement spacers and their particular construction.

The first step of the surgical procedure is to determine what height of prosthetic cement spacer is desired for a particular patient and a particular set of anatomical conditions. Once this height has been selected, it is important to next determine whether the spacer style with the smooth-surfaced pointed wire 22 is preferred or whether the rolled thread pointed wire 37 style should be used. The next step is to prepare the acetabulum by reaming the generally spherical bone surface to a spherical diameter size which is generally equal to the sum of the acetabular cup diameter plus twice the height 26 of the selected prosthetic cement spacers. In this manner, the acetabulum will be prepared with an increased size in order to accommodate the additional height or thickness of the standoff body portion and yet still position the acetabular cup in the correct location. For example, if a 3 mm prosthetic cement spacer height is selected, then a reamer must be used which has a diameter that is 6 mm greater than the external diameter of the acetabular component being used, such as acetabular cup 47. For example, a 52 mm diameter acetabular cup will require a 58 mm diameter reamer.

During this reaming procedure, the acetabular cup may be placed in position to check for evenness of reaming and correct alignment. Next, the prosthetic cement spacers 20 are gas sterilized prior to their insertion into the bone surface of the acetabulum. The preferred location for the equilateral triangle grouping of three cement spacers is approximately midway between center point 50 and rim 51. However, such a positional choice orients the prosthetic spacers at an approximately midway location up the external surface of the acetabular cup and in some situations the cup has its own surface contouring to facilitate or enhance its bonding or securing into position. In such situations where the cup is contoured in the area where the spacers contact, this spacer location will interfere with the purposes of the contouring. Therefore, it is generally considered that the equilateral triangle grouping should be oriented in the inner one-third of the acetabulum surface. With the equilateral triangle arrangement of the three prosthetic cement spacers inserted full depth into the acetabulum bone surface, the acetabular cup is then tried. Any misalignment or rocking may be compensated for by relocation of one or more of the spacers or by shape modification to these spacers. A further aspect of this equilateral triangle arrangement is that one cement spacer 20 be inserted into the ischium bone portion, that another be inserted into the ilium bone portion and that the third be inserted into the pubis bone portion. Once the final orientation of the three cement spacers has been determined and the acetabular cup positioned and aligned, it is important that the acetabulum be cleaned prior to placement of the acrylic bone cement into the interface. The standoff body portion 21 is fabricated out of acrylic bone cement of the type normally supplied for surgical use and the pointed wire is fabricated out of a steel alloy, such as stainless steel, and these two materials are known to be biocompatible. It is also known that the surface of the polymerized acrylic bone cement of the standoff body portion repolymerizes when the new acrylic bone cement is introduced. Thus, the nature of the bond formed between the new acrylic bone cement and the acrylic bone cement of the standoff body portion should eliminate stress concentrations at the interface.

It is desirable that the acrylic bone cement be used in a more liquid form than normal in order to insure proper repolymerization with the standoff body portion 21 of the spacers 20. Care should also be taken to handle the spacers with instruments rather than with the surgical gloves in order to prevent coating the standoff body portion's exterior surface with contaminant materials which could impede the repolymerization process. After the acrylic bone cement has been placed into position over and around the various cement spacers, the acetabular cup is manually pushed into position until it is felt to rest against the top surfaces of these cement spacers. At this time, it is possible to firmly hold the acetabular cup in place, an activity that a surgical assistant can perform, thus allowing the orthopedic surgeon to use both hands to smooth and effectively pack the cement around the acetabular cup. When this packing is completed, the area is trimmed and a smooth surface formed.

This method is a simple and reliable one which allows the surgeon to produce a predictable and desired thickness of cement surrounding a joint replacement component. It is not only a desirable and helpful method of producing standard thicknesses of acrylic bone cement, but since the component can be held rigidly in place, better packing of the cement around the prosthetic member occurs. The components are compatible and in general the method disclosed should lead to more predictable end results in the field of joint replacement surgery.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic cement spacer for controlling the thickness of cement applied between a prosthetic insert and a supporting member to which the insert is to be secured, such as a natural bone, said prosthetic cement spacer comprising:

a standoff body fabricated from biocompatible acrylic bone cement which is solid and substantially cylindrical and having a top surface and a base surface; and means for anchoring said standoff body to said supporting member, said anchoring means including a pointed wire having a received portion secured within said standoff body and an extending portion free of said standoff body, the length of said free portion being at least as great as the length of said received portion, said extending portion extending outwardly from said base surface, and being substantially concentric to said standoff body.

* * * * *